United States Patent
Csutak et al.

(10) Patent No.: US 10,429,350 B2
(45) Date of Patent: Oct. 1, 2019

(54) PHOTOACOUSTIC GAS DETECTION

(71) Applicant: Saudi Arabian Oil Company, Dhahran (SA)

(72) Inventors: Sebastian Csutak, Houston, TX (US); Weichang Li, Katy, TX (US); Angelo Sampaolo, Houston, TX (US); Gregory Ham, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/031,790

(22) Filed: Jul. 10, 2018

(65) Prior Publication Data

US 2019/0017966 A1    Jan. 17, 2019

Related U.S. Application Data

(60) Provisional application No. 62/531,050, filed on Jul. 11, 2017.

(51) Int. Cl.
*G01N 29/02* (2006.01)
*G01N 29/22* (2006.01)
(Continued)

(52) U.S. Cl.
CPC ......... *G01N 29/022* (2013.01); *E21B 49/081* (2013.01); *G01N 21/1702* (2013.01);
(Continued)

(58) Field of Classification Search
CPC ............... G01N 2021/1704; G01N 29/228
(Continued)

(56) References Cited

U.S. PATENT DOCUMENTS

| 4,051,372 A * | 9/1977 | Aine | B01D 53/22 |
| | | | 250/255 |
| 7,317,989 B2 * | 1/2008 | DiFoggio | E21B 47/10 |
| | | | 166/264 |

(Continued)

OTHER PUBLICATIONS

Ono et al., "Measurement of a Doubly Substituted Methane Isotopologue, 13CH3D, by Tubable Infrared Laser Direct Absorption Spectroscopy," Analytical Chemistry, vol. 86, Jun. 2014, 8 pages.

(Continued)

*Primary Examiner* — Daniel S Larkin
(74) *Attorney, Agent, or Firm* — Fish & Richardson P.C.

(57) ABSTRACT

A downhole system includes a quartz enhanced photoacoustic spectrometer (QEPAS) configured to be positioned within a wellbore formed in a subterranean zone of a hydrocarbon formation, a sampling system coupled to the QEPAS, and a computer system connected to the QEPAS. The sampling system is configured to be positioned in the wellbore and obtain a sample of a wellbore fluid at a downhole location in the subterranean zone. The QEPAS is configured to spectroscopically scan the sample and to determine a plurality of quantities of a corresponding plurality of hydrocarbons in the same. The computer system includes one or more processors to perform operations including receiving the plurality of quantities of the plurality of hydrocarbons in the sample and determining a plurality of ratios, where each ratio is a ratio of one of the plurality of hydrocarbons with another of the plurality of hydrocarbons.

13 Claims, 9 Drawing Sheets

(51) Int. Cl.
  *G01N 29/24* (2006.01)
  *G01V 1/44* (2006.01)
  *E21B 49/08* (2006.01)
  *G01N 29/46* (2006.01)
  *G01N 21/17* (2006.01)

(52) U.S. Cl.
  CPC ....... *G01N 29/228* (2013.01); *G01N 29/2418* (2013.01); *G01N 29/46* (2013.01); *G01V 1/44* (2013.01); *G01N 2021/1704* (2013.01)

(58) Field of Classification Search
  USPC .............................................. 73/24.02, 24.06
  See application file for complete search history.

(56) References Cited

U.S. PATENT DOCUMENTS

| | | | |
|---|---|---|---|
| 7,387,021 | B2 | 6/2008 | DiFoggio |
| 7,520,158 | B2 | 4/2009 | DiFoggio |
| 8,098,376 | B2 | 1/2012 | So et al. |
| 8,334,980 | B2 | 12/2012 | So et al. |
| 8,359,904 | B2 | 1/2013 | Nicoletti et al. |
| 9,696,283 | B1 * | 7/2017 | Yu ........................ G01N 29/02 |
| 2006/0266108 | A1 | 11/2006 | DiFoggio |
| 2006/0266109 | A1 | 11/2006 | Difoggio |
| 2009/0027677 | A1 | 1/2009 | Willing et al. |
| 2010/0011836 | A1 * | 1/2010 | Kalkman ........... G01N 21/1702 73/24.02 |
| 2011/0072886 | A1 * | 3/2011 | Caneau .............. G01N 21/1702 73/24.02 |
| 2012/0151994 | A1 * | 6/2012 | Hung ................. G01N 21/1702 73/24.02 |
| 2012/0210796 | A1 * | 8/2012 | Schade ............. G01N 21/1702 73/655 |
| 2014/0138528 | A1 | 5/2014 | Pope et al. |
| 2016/0018985 | A1 | 1/2016 | Bennet et al. |
| 2016/0054285 | A1 * | 2/2016 | Freese ...................... G01J 3/40 356/70 |
| 2016/0139085 | A1 | 5/2016 | Pelletier et al. |
| 2017/0038294 | A1 * | 2/2017 | Kshirsagar ......... G01N 21/1702 |

OTHER PUBLICATIONS

Douglas et al., "Methane clumped isotopes: Progress and potential for a new isotopic tracer," Organic Geochemistry vol. 113, Nov. 2017, 21 pages.

International Search Report and Written Opinion issued in International Application No. PCT/US2018/041299 dated Sep. 20, 2018, 18 pages.

* cited by examiner

PHOTOACOUSTIC GAS DETECTION

CROSS-REFERENCE TO RELATED APPLICATION(S)

This application claims the benefit of priority to U.S. Provisional Application Ser. No. 62/531,050, filed Jul. 11, 2017, the contents of which are hereby incorporated by reference.

TECHNICAL FIELD

This specification relates to hydrocarbon gas detection in reservoirs using photoacoustic spectroscopy.

BACKGROUND

Commercial-scale hydrocarbon production from source rocks and reservoirs requires significant capital. It is therefore beneficial to obtain as much accurate data as possible about a formation in order to assess its commercial viability and subsequently to optimize cost and design of development. Hydrocarbon monitoring—especially of methane, ethane, and propane—can be used to predict production, estimate reserves, and assess raw material quality of source rocks and reservoirs. Exploration, reservoir design, and petrochemical manufacturing design are only a few of the many areas that can benefit from comprehensive hydrocarbon monitoring data.

SUMMARY

This specification relates to hydrocarbon gas detection in reservoirs using photoacoustic spectroscopy. Certain aspects of the subject matter described here can be implemented as a system. A downhole system includes a quartz enhanced photoacoustic spectrometer (QEPAS) configured to be positioned within a wellbore formed in a subterranean zone of a hydrocarbon formation, a sampling system coupled to the QEPAS, and a computer system connected to the QEPAS. The sampling system is configured to be positioned in the wellbore and obtain a sample of a wellbore fluid at a downhole location in the subterranean zone. The QEPAS is configured to spectroscopically scan the sample and to determine a plurality of quantities of a corresponding plurality of hydrocarbons in the same. The computer system includes one or more processors and a computer-readable medium storing instructions executable by the one or more processors to perform operations including receiving the plurality of quantities of the plurality of hydrocarbons in the sample and determining a plurality of ratios, where each ratio is a ratio of one of the plurality of hydrocarbons with another of the plurality of hydrocarbons.

This, and other aspects, can include one or more of the following features. The operations can include receiving the plurality of ratios as an input to a design simulation of the hydrocarbon formation and computationally simulating the hydrocarbon formation based, in part, on the plurality of ratios. The QEPAS can include a laser that can be configured to emit light at a wavelength range at which the plurality of hydrocarbons in the sample are simultaneously detectable. The QEPAS can include a plurality of lasers, and each laser can be configured to emit light at a respective wavelength at which a respective hydrocarbon of the plurality of hydrocarbons in the sample is detectable. The QEPAS can include a hydrogen sulfide ($H_2S$) laser that can be configured to emit light at a wavelength at which $H_2S$ in the sample is detectable. The QEPAS can include a quartz tuning fork (QTF) that can be configured to detect a pressure wave created in a gas in the sample and a laser configured to emit light, and the pressure wave can be created as the light is absorbed by the gas. The QEPAS can include a signal modulator that can be configured to periodically switch a laser injection current to the laser between an on state and an off state or an optical chopper to optically chop the light emitted by the laser. The signal modulator can be configured to generate a periodic function to modulate a frequency of the light. The quality factor (Q factor) of the QTF can be on the order of tens of thousands. The QTF can be a first, passive QTF. The QEPAS can include a second, active QTF configured to induce a pressure wave in the gas, and the first, passive QTF can be configured to detect the induced pressure wave.

The system can include a power source connected to the processor, and the power source can be configured to drive the second, active QTF in response to receiving a signal from the processor. The processor can be configured to transmit the signal to the second, active QTF based on a signal received from the first, passive QTF. The system can include a temperature controller configured to maintain a temperature of the QEPAS. The sampling system can include a chamber, a piston positioned within the chamber, an inlet valve fluidically connected to a chamber inlet, and an outlet valve fluidically connected to a chamber outlet. The piston can seal an inner surface of the chamber to define a sample receiving volume, where the QTF can be positioned within the sample receiving volume. A retraction of the piston in the sample receiving volume and an opening of the inlet valve can cause the sample to flow into the sample receiving volume. An advancement of the piston in the sample receiving volume and an opening of the outlet valve can cause the sample to flow out of the sample receiving volume. The sample can be a two-phase sample including a gas and a liquid. The inlet valve can be configured to de-pressurize the sample to separate the gas from the liquid, and the gas can rise to an upper portion of the sample receiving volume while the liquid can reside in a lower portion of the sample receiving volume. The QEPAS can be configured to spectroscopically scan the gas in the upper portion.

Certain aspects of the subject matter described here can be implemented as a method. A quartz enhanced photoacoustic spectrometer (QEPAS) is positioned at a downhole location within a wellbore formed in a subterranean zone of a hydrocarbon formation. A sample of a wellbore fluid at the downhole location in the subterranean zone is obtained, and the sample is spectroscopically scanned using the QEPAS at the downhole location. A plurality of quantities of a corresponding plurality of hydrocarbons in the sample are determined, and a plurality of ratios, each ratio being a ratio of one of the plurality of hydrocarbons with another of the plurality of hydrocarbons, are determined.

This, and other aspects, can include one or more of the following features. The method can include computationally simulating the hydrocarbon formation based, in part, on the plurality of ratios. Spectroscopically scanning the sample can include emitting light from a single laser to simultaneously detect the plurality of hydrocarbons. Spectroscopically scanning the sample can include emitting a plurality of rays of light from a corresponding plurality of lasers, where each laser can be configured to detect a hydrocarbon of the plurality of hydrocarbons. Spectroscopically scanning the sample can include modulating light emitted by a laser that can be configured to detect the plurality of hydrocarbons.

The details of one or more implementations of the subject matter described in this specification are set forth in the accompanying drawings and the following description. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure describes systems for detecting hydrocarbon gas in reservoirs using photoacoustic spectroscopy. Extracting hydrocarbons from a source rock or a reservoir involves drilling a borehole into the earth with a rotating drill bit attached to a drill string. Downhole devices can take measurements of subterranean operating parameters and various fluid characteristics. Downhole devices that take measurements during the drilling process can be referred to as logging-while-drilling (LWD) or measurement-while-drilling (MWD) devices, while downhole devices that take measurements after drilling can be referred to as wireline logging devices.

Information gathered from a subterranean zone with these devices can be analyzed to evaluate and map a hydrocarbon formation. The analysis can be used to guide well placement, also referred to as geo-steering, so that the wellbore remains within a zone of interest or in the most economically productive portion of a reservoir. Therefore, these devices have helped facilitate the shift of well construction from geometrical designs to designs steered by geological information and have also been utilized to successfully design wells with deviation, extended-reach, and horizontal boreholes to extract hydrocarbons from more difficult and marginal reservoirs. These devices are valuable not only for making informed wellsite decisions, but also for long-term reservoir planning and development.

Figure 1:
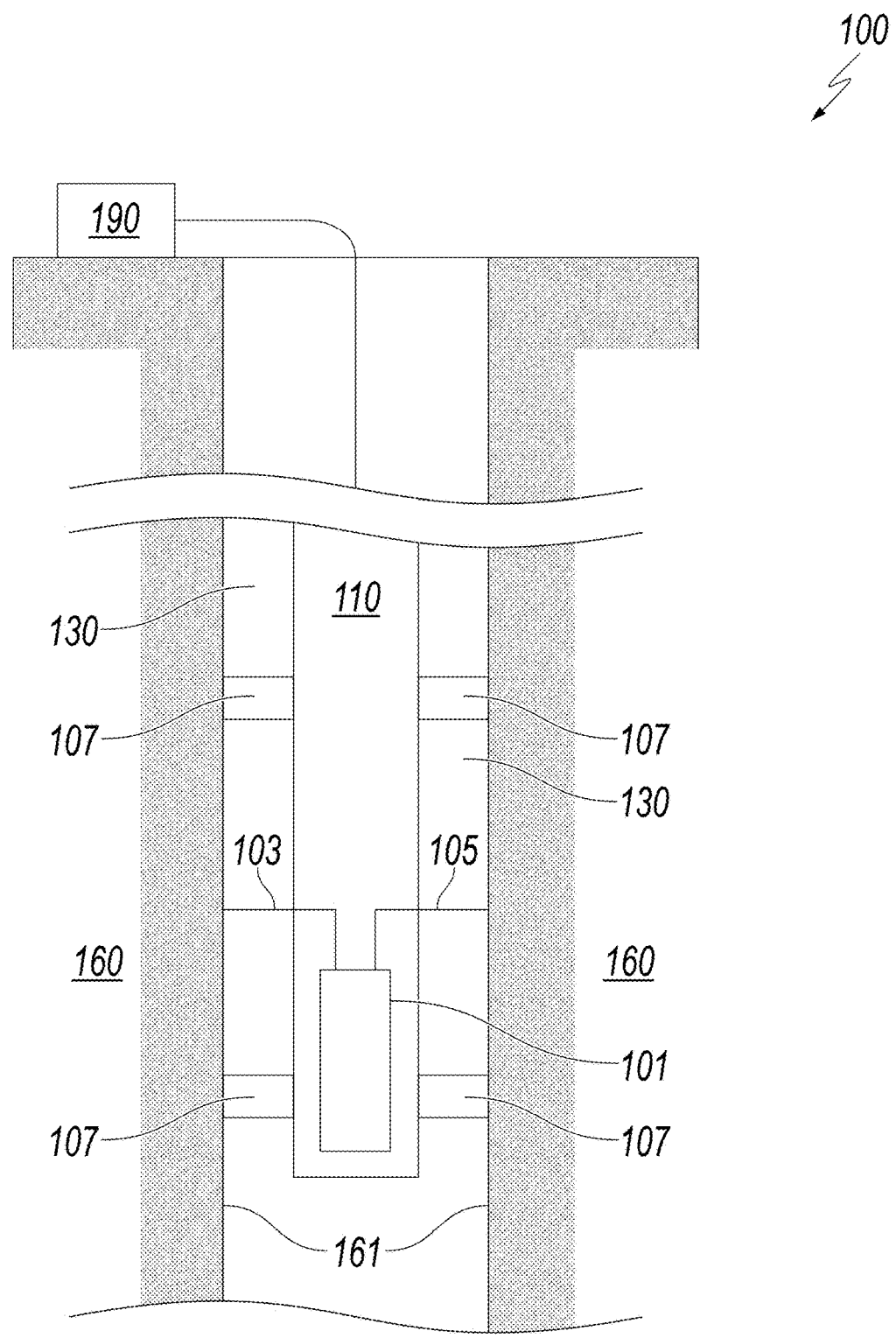
FIG. 1 is a schematic diagram of an example downhole gas detection system.

FIG. 1 is a schematic diagram of an example downhole gas detection system 100. The gas detection module 101 can travel down and be positioned along a drill string 110 within a wellbore 161 formed in a subterranean zone of a hydrocarbon formation. The drill string 110 can be supported by packers or anchors 107 at various points along the wellbore 161. The gas detection module 101 includes a quartz enhanced photoacoustic spectrometer (QEPAS) system 200 (described later) and a sampling system 400 (described later) that can be coupled to the QEPAS system 200. The gas detection system 100 as shown in FIG. 1 is shown as being implemented in a vertical orientation. The gas detection system 100 can also be implemented in horizontal and slanted wellbores. The gas detection module 101 can be positioned in the wellbore 161 and obtain a sample of a wellbore fluid at a downhole location in the subterranean zone, such as a wellbore annulus 130 or a rock formation 160. The gas detection module 101 can spectroscopically scan the sample and determine multiple quantities of corresponding hydrocarbons in the sample. The gas detection module 101 can allow fluid to enter through an inlet line 103 and to exit through an outlet line 105.

Still referring to FIG. 1, the gas measurement data from the gas detection module 101 is sent to a surface process 190. The gas detection module 101 can spectroscopically scan a gas sample and measure the composition of various hydrocarbons, such as methane ($C_1$), ethane ($C_2$), propane ($C_3$), butane ($C_4$), and their isotopologues, in a wellbore fluid. The hydrocarbon isotopologues can include carbon isotopes such as $^{13}C$ or $^{12}C$. The hydrocarbon isotopologues can include hydrogen isotopes such as deuterium (D). Some non-limiting examples of hydrocarbon isotopologues are $^{13}CH_3D$, $^{12}CH_3D$, $^{12}CH_4$, and $^{12}CH_2D_2$. The surface process 190 includes a computer system 800 (described later) that includes a processor and a computer-readable medium that can store instructions executable by the processor in order to receive quantities of hydrocarbons in the sample, analyze the various hydrocarbons, and determine hydrocarbon ratios, such as ratio of $C_1/C_4$, and isotopic ratios, such as $^{13}C/^{12}C$, of a wellbore fluid. The surface process 190 includes incorporating the obtained and manipulated data such as hydrocarbon ratios as input to a mapping, model, or design simulation of a hydrocarbon formation or reservoir. The mapping, model, or simulation, which can be based on multiple hydrocarbon ratios at various locations in the wellbore, can be computational and can be utilized to forecast field performance and production of the formation or reservoir.

Figure 2:
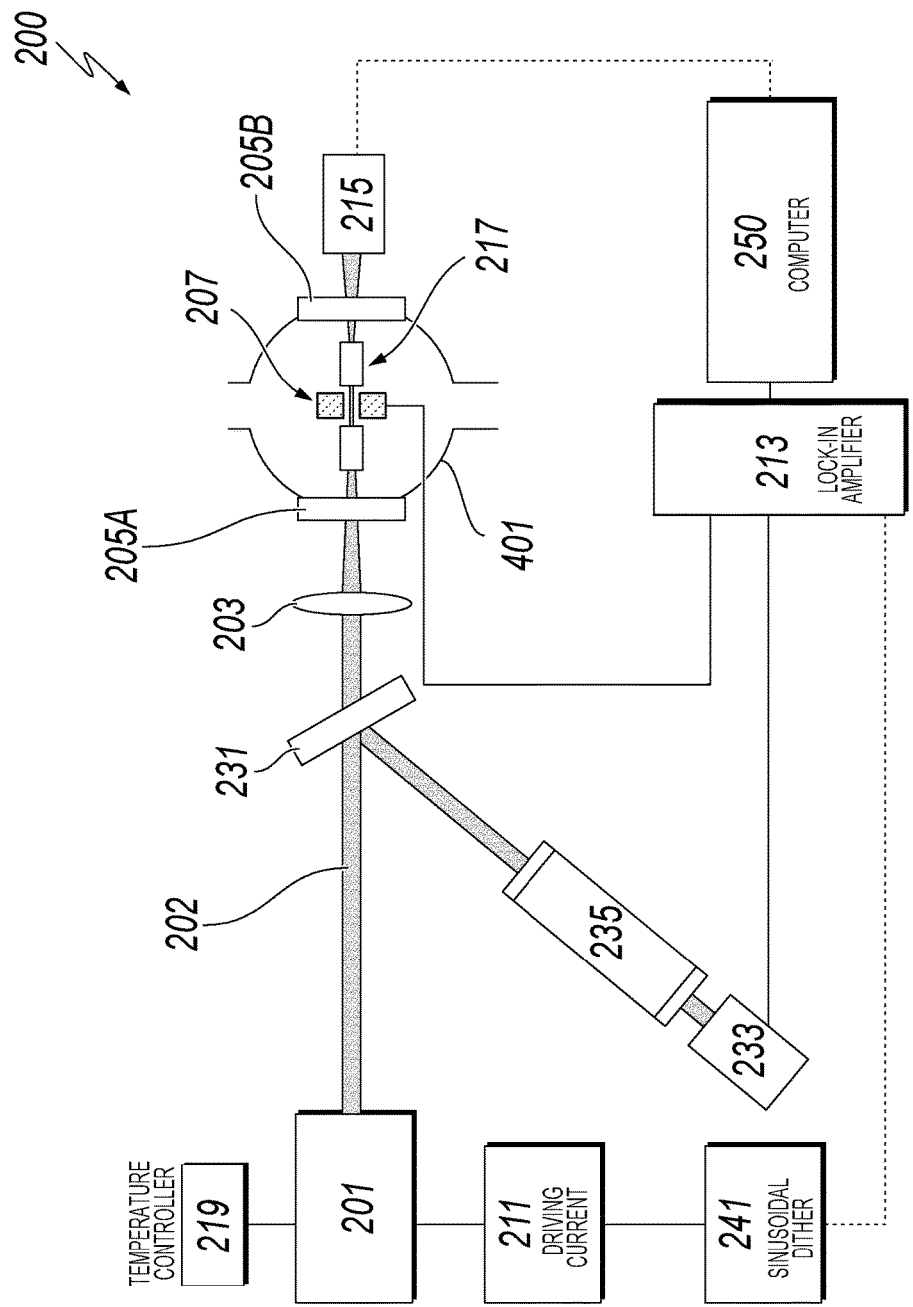
FIG. 2 is a schematic diagram of an example photoacoustic spectroscopy system.

FIG. 2 is a schematic diagram of an example of a QEPAS system 200 for the downhole gas detection module 101. The QEPAS system 200 detects gases utilizing a laser 201 and a quartz tuning fork (QTF) 207 as a detector for a pressure wave induced or created in a gas. The QEPAS system 200 can detect gas composition with sensitivities on the level of parts per trillion (ppt) due to the characteristically large quality factor (Q factor) of the QTF, for example, a Q factor on the order of tens of thousands (10,000) at normal atmospheric pressure. Conventional laser-based spectroscopic techniques, such as tunable diode laser absorption spectroscopy or cavity ring down spectroscopy, typically utilize photodetectors or photodiodes that require a cooling system, such as a thermoelectric or nitrogen-based cooling system, and can be relatively large in size. In some implementations, the QEPAS system 200 is independent of a cooling system, and the laser utilized in the QEPAS system 200 can be tailored to operate at elevated temperatures, such as approximately 45 degrees Celsius (° C.) to 200° C., which is typically characteristic of downhole applications. The QEPAS system 200 can therefore be applied as a portable gas detection system at a wellsite or in the borehole (wireline or LWD).

The QEPAS system 200 includes a tunable laser 201, which can be a distributed feedback (DFB) quantum cascade laser (QCL), external cavity (EC) QCL, or interband cascade laser (ICL), that emits a laser beam 202. Examples of lasers include indium arsenide antimonide (InAsSb) lasers with wavelengths of approximately 1800 to 3000 nanometers (nm), indium gallium arsenide phosphide (InGaAsP) lasers typically used in telecommunication with wavelengths of approximately 1300 to 1700 nm, which can be used for methane detection, and other similar lasers for hydrogen sulfide ($H_2S$). DFB lasers can be suitable candidates for the QEPAS system 200 as they typically have narrow laser beam 202 widths. Typically, the wavelength (and concurrently, the frequency) of the laser is varied by changing the driving current 211. The QEPAS system 200 can optionally include a temperature controller 219 to maintain the temperature greater than a borehole temperature. For example, a production field temperature could be approximately 90° C., so the controller 219 could maintain the QEPAS system 200 temperature at approximately 95° C. The laser beam passes through a lens 203 and enters a chamber 401 through a window 205A. The chamber 401 contains a gas to be tested, for example, a mixture of hydrocarbons and water vapor. As the laser beam 202 travels through the gas, some light is absorbed by the gas sample, and a pressure wave is induced or created in the gas sample. The QEPAS system 200 includes a quartz enhanced tuning fork (QTF) 207 that can detect a pressure wave created in a gas sample. The laser 201 can be tuned to a selected frequency and emit light through the gas such that the gas absorbs some of the light and gets heated, thereby creating a small pressure wave, for example, in a range of approximately $10^{-8}$ torr to approximately $10^{-3}$ torr. The pressure wave can be detected by the QTF 207 as the laser beam 202 travels between prongs of the QTF 207. In some implementations, the laser 201 is modulated at half the resonance frequency of the QTF 207. The response from the QTF 207 is processed by a lock-in amplifier 213, which demodulates the QEPAS signal at the QTF resonance frequency. The resonance frequencies can vary from 32 kilohertz (kHz) for standard tuning forks typically employed for timing applications, down to a few kHz (for example, approximately 1 kHz or in a range of approximately 1 kHz to approximately 9 kHz) for custom tuning forks devoted to gas spectroscopy. Then the signal is acquired and analyzed by a processor or computer 250.

These components can vary depending on the spectral range and targeted molecule in the gas sample. In some implementations, the QEPAS laser 201 can emit light at a wavelength range at which multiple hydrocarbons can be detected simultaneously within a sample because of its wide laser (light) wavelength tuning range, for example, approximately 8 nm. In some implementations, the QEPAS system 200 can be designed to includes multiple lasers if the spectral range covered by the hydrocarbons absorption features is too wide. Multiple laser chips can be packaged on a carrier, and multiple beam splitters can be used to couple the lasers with the tuning fork. In the case with multiple lasers, each laser can be driven one at a time, such that the response of the fork can be acquired from a sample. Each laser can emit light at a respective wavelength corresponding to a molecule such as a hydrocarbon detectable in the sample, for example, one laser for methane and one laser for propane. The QEPAS system 200 can optionally include a dedicated $H_2S$ laser configured to emit light at a wavelength at which $H_2S$ is detectable in the sample gas. A sinusoidal dither 241 can be applied in tuning the laser 201.

In some implementations, the laser beam 202 is split by a beam-splitter 231, and a portion of the laser beam 202 is sent to a photodetector 233 through a reference cell 235 containing a concentration of the target gas. The photodetector 233 can send a signal to the lock-in amplifier 213 and pass to the processor or computer 250 where the signal is processed, and the results can be used to tune the laser 201.

The QEPAS system 200 can optionally include a photodetector 215 to tune the laser 201. The laser beam 202 can exit the chamber 401 through a window 205B and be detected by the photodetector 215. The photodetector 215 can send a signal to the processor or computer 250 where the signal is processed, and the results can be used to tune the laser 201. The QEPAS system 200 can optionally include micro-resonator tubes 217 which can enhance the QEPAS signal and confine the induced pressure wave. The micro-resonator tubes 217 can include two thin tubes aligned perpendicular to the QTF 207 plane, in line with the laser beam 202, and carefully positioned, so that the laser beam 202 enters the micro-resonator tubes 217, but does not touch the walls of the micro-resonator tubes 217 in order to avoid photothermal effects.

Figure 3:
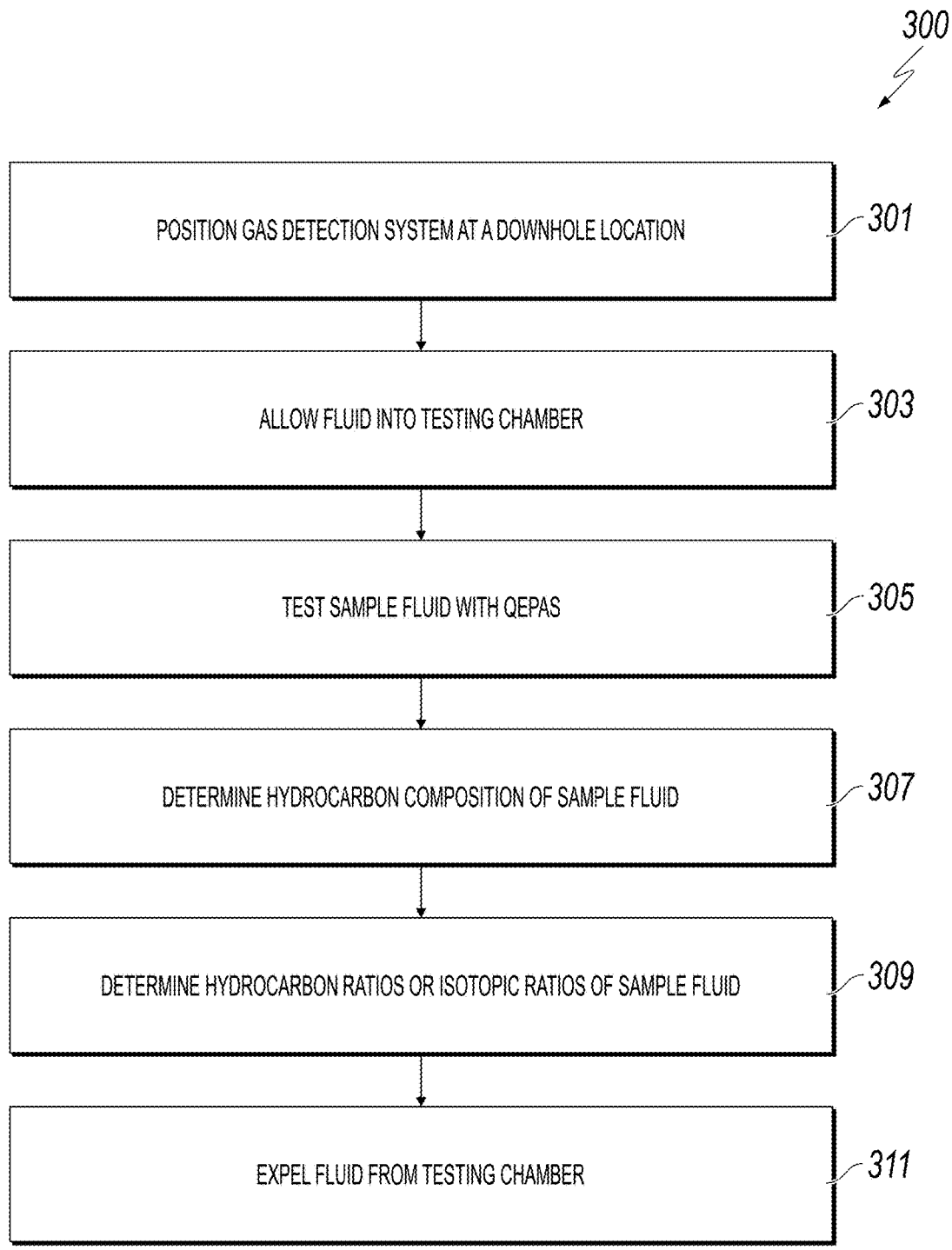
FIG. 3 is a flow chart illustrating an example method for downhole gas detection.

FIG. 3 is a flow chart of an example method 300 for detecting gases downhole. At step 301, a gas detection module, such as the gas detection module 101 shown in FIG. 1, is positioned at a downhole location. Positioning the gas detection module can include lowering the gas detection module 101 into a borehole with an electrical cable after drilling, which is characteristic of wireline logging. The gas detection module 101 can optionally be a component of a drill collar in a bottomhole assembly, in which case the module 101 travels along a wellbore while drilling occurs, which is a characteristic of LWD or MWD devices. In the case the gas detection module 101 is a component of the bottomhole assembly, the module 101 can take measurements at various depths and points of a reservoir as a well is drilled.

Once the gas detection module 101 is located at a desired point downhole, the gas detection module 101 allows borehole fluid into a testing chamber 401 of the module 101 at step 303. The fluid can be extracted from a wellbore annulus 130 or a rock formation 160. Once a desired volume of fluid is allowed into the testing chamber 401, the gas detection module 101 can be isolated to prevent fluid from entering or exiting the testing chamber 401. At step 305, the fluid in the chamber 401 is tested with a QEPAS system, such as the QEPAS system 200 shown in FIG. 2. At step 307, a surface process 190 which includes a computer system 800 can determine the quantities of several hydrocarbons in the sample, such as methane and propane. At step 309, the computer system 800 can determine the ratios of several hydrocarbons in the sample, such as $C_1/C_3$ ratio. The computer system 800 can also determine the ratios of carbon isotopes in a sample, such as $^{13}C/^{12}C$. After the fluid is tested, the fluid is expelled from the chamber 401 at step 311. Once the chamber 401 is evacuated, the method 300 can cycle to step 301 at another downhole location. The surface process steps 307 and 309 can optionally be completed after sampling data has been compiled at various downhole points because the data can be coupled with depth or location data that can later be used to model or simulate a formation and also to develop the design of a reservoir.

Figure 4A:
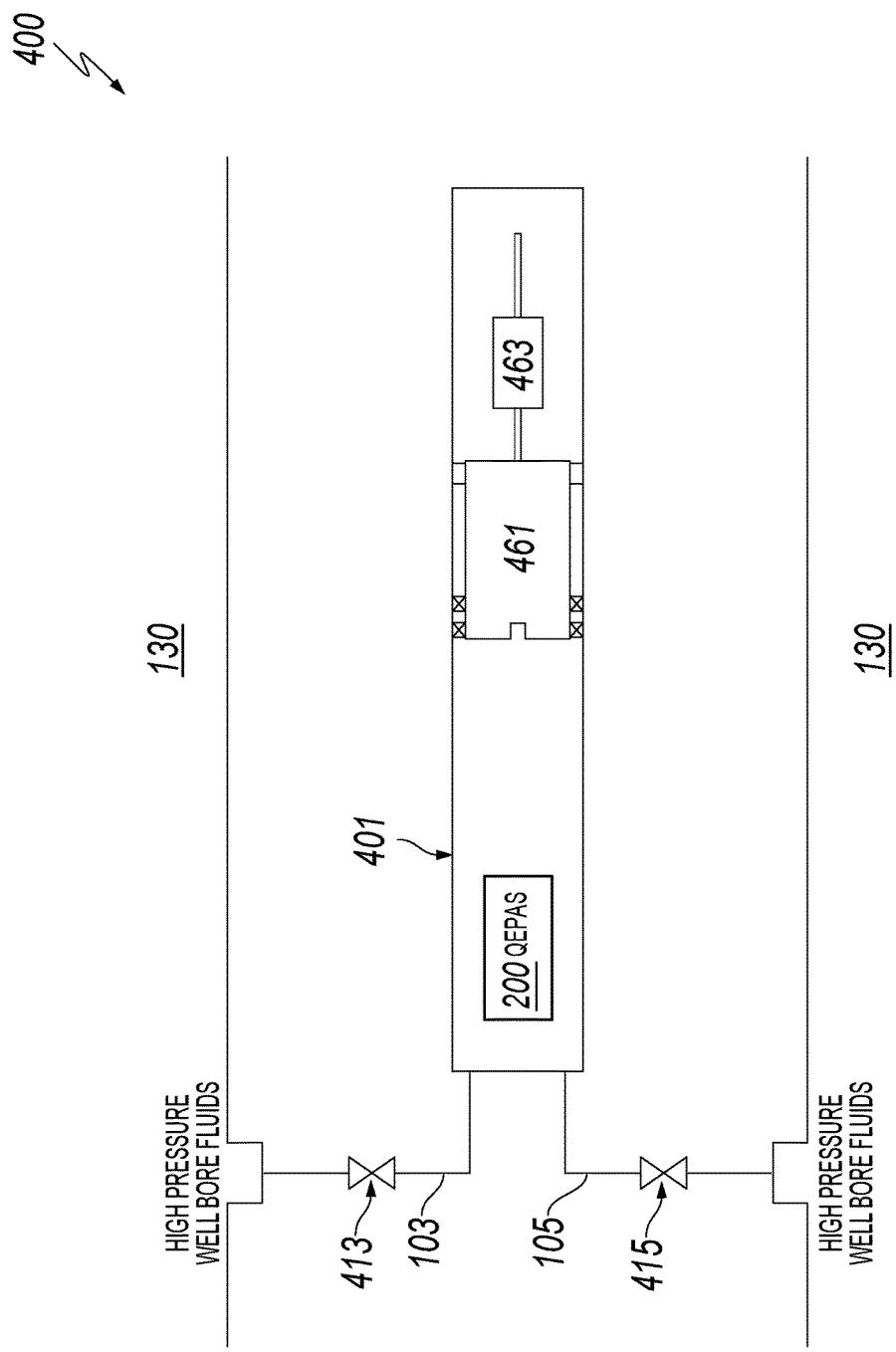
FIG. 4A is a schematic diagram of an example sampling system.

FIG. 4A is a schematic diagram of an example of a sampling system 400 for the downhole gas detection module 101. The sampling system 400 can include a chamber inlet line 103, an inlet valve 413, a chamber outlet line 105, an outlet valve 415, a chamber 401, a piston 461, and a piston actuator 463. The inlet valve 413 can open to allow a fluid to flow through the chamber inlet line 103 and into the sample receiving volume of the chamber 401. The chamber inlet 103 can be configured to bring in fluid from the wellbore annulus 130 (as shown) or the rock formation 160.

The outlet valve 415 can open to allow a fluid to travel out of the sample receiving volume of the chamber 401 and through the chamber outlet line 105. The chamber outlet 105 can be configured to expel fluid to the wellbore annulus 130 (as shown) or the rock formation 160. The chamber 401 can have a cylindrical or cuboidal shape. For example, the chamber 401 can be cylindrical with a diameter in a range of approximately 0.38 inches (in) to 3.63 in and a length in a range of approximately 4 in to 96 in. The piston 461 seals an inner surface of the chamber 401, which determines the sample receiving volume in the chamber 401. For example, the piston 461 can be a cylinder and have grooves for seals that close off the space between the piston 461 and the walls of the chamber 401. The volume can be varied by retracting or advancing the piston 461 with the actuator 463. The actuator 463 can utilize, for example, mechanical screw drives, pressure actuation, or driven gears. In relation to the QEPAS system 200 (shown in FIG. 2), the QTF 207 can be located in the upper portion of the chamber 401, and the laser beam 202 produced by the laser 201 can pass through the chamber 401 and between the prongs of the QTF 207.

Figure 4B:
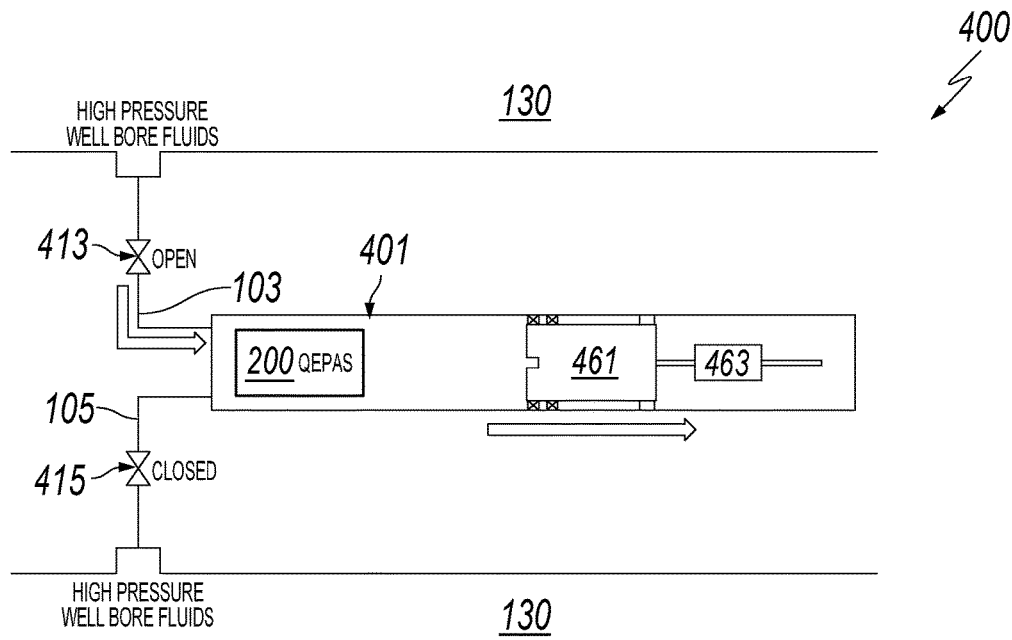
FIGS. 4B & 4C are flow diagrams of fluid movement in an example sampling system.
Figure 4C:
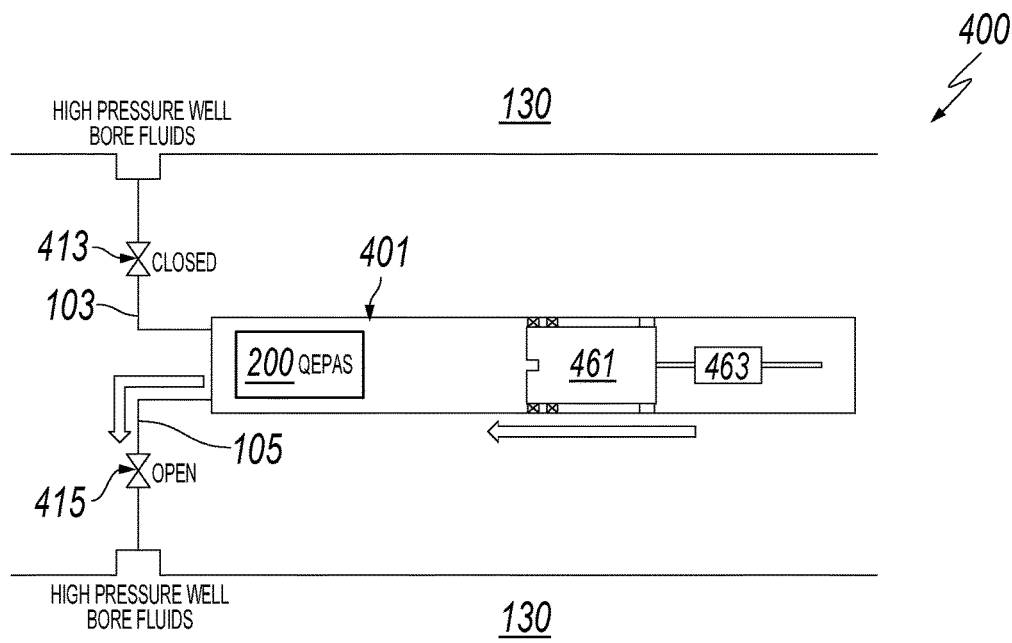

FIGS. 4B and 4C illustrate the movement of fluid through the sampling system 400 for the downhole gas detection module 101. Referring to FIG. 4B, to bring fluid into the chamber 401, the inlet valve 413 can be opened partially or fully, the outlet valve 415 can be closed, and the piston 461 can be retracted by the actuator 463 to increase the volume of the chamber 401. Referring to FIG. 4C, to expel fluid out of the chamber 401, the outlet valve 415 can be opened partially or fully, the inlet valve 413 can be closed, and the piston 461 can be advanced by the actuator 463 to decrease the volume of the chamber 401.

Figure 5:
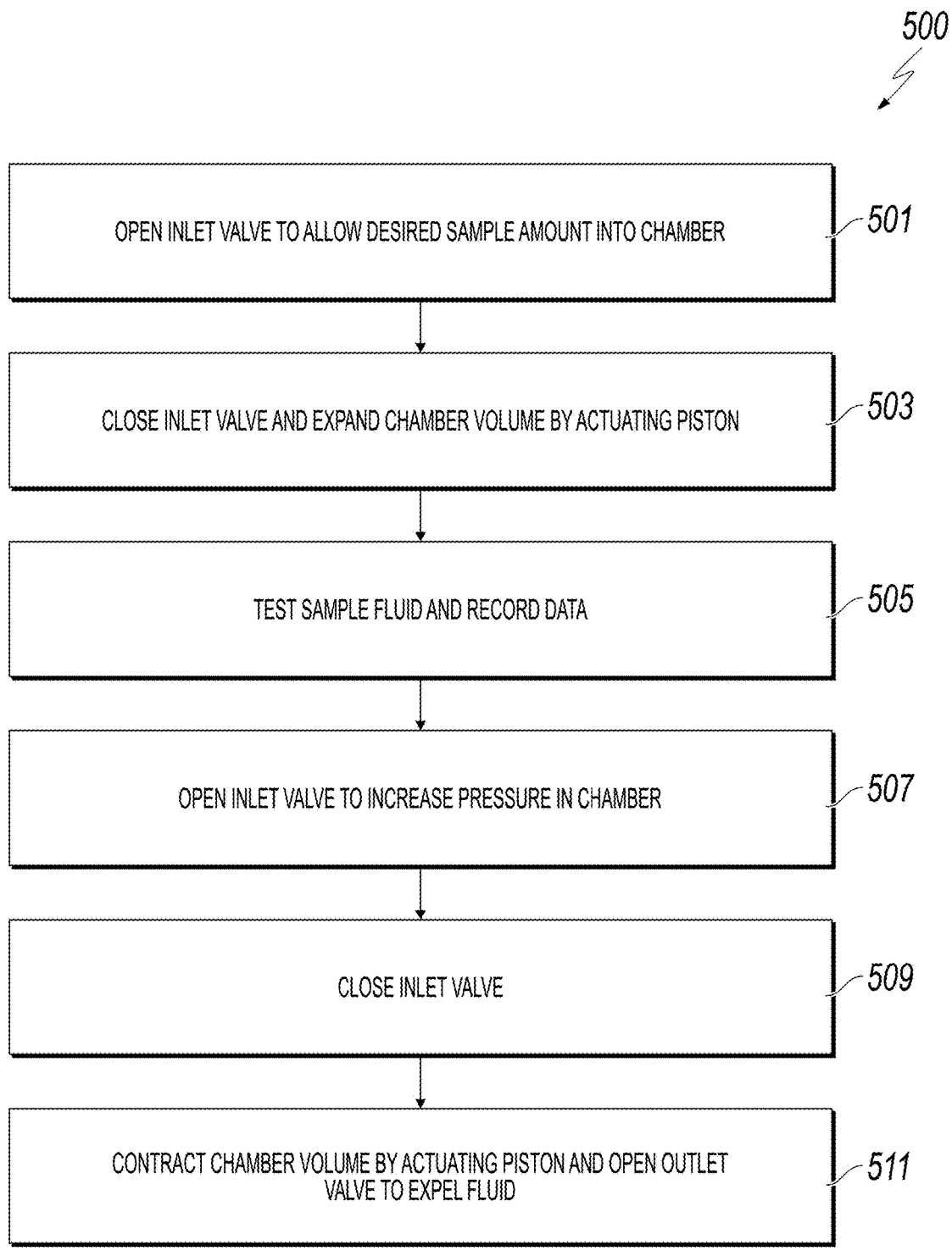
FIG. 5 is a flow chart illustrating an example method for downhole gas sampling.

FIG. 5 is a flow chart of an example method 500 for sampling a downhole fluid. At step 501, the inlet valve 413 is opened to allow a desired amount of fluid into the chamber 401. The sample can have multiple phases. For example, the sample can be a two-phase sample of liquid and gas. As the fluid travels through the inlet valve 413, the sample fluid can de-pressurize. In other words, the fluid's pressure can be reduced as it travels through the inlet valve 413. The reduction in pressure can cause the fluid to flash (evaporate) across the inlet valve 413. At step 503, the inlet valve 413 is closed to stop flow of fluid into the chamber 401. The volume of the chamber 401 is increased by retracting the piston 461 with the actuator 463. The increase in volume of the chamber 401 further reduces the pressure inside the chamber 401. The resulting pressure inside the chamber 401 can be close to atmospheric pressure, for example, 0 pounds per square inch gauge (psig). As a result of the decreased pressure in the chamber 401, a majority of the fluid is vapor. For example, the liquid phase of the fluid can make up 0% to 4% of the volume of the chamber 401. Any liquid within the chamber 401 travels to a lower portion of the sample receiving volume in the chamber 401 and can optionally be drained before the fluid is tested. The vapor or gas can rise to an upper portion of the sample receiving volume in the chamber 401. At step 505, the fluid can be tested, for example, by the QEPAS system 200, and the data can be recorded. The QEPAS system 200 can be configured to spectroscopically scan the sample gas in the upper section of the chamber 401. Once testing is complete, the inlet valve 413 is opened to allow additional fluid to enter the chamber 401 at step 507. At downhole locations, the pressure of borehole fluid can be, for example, 6,000 psig or greater. By allowing additional borehole fluid to enter the chamber 401, the pressure in the chamber 401 can increase to equal the borehole pressure. At step 509, the inlet valve 413 is closed.

At step 511, the outlet valve 415 is opened, and the volume of the chamber 401 is decreased by advancing the piston 461 with the actuator 463. The decrease in volume of the chamber 401 increases the pressure within the chamber 401 and allows fluid to travel out of the chamber 401 through outlet valve 415. The method 500 can cycle to step 501 at another downhole location or at the same location in the case that multiple data runs are desired. At another downhole location, the gas detection module 101 can optionally cycle through allowing fluid into the chamber 401 and expelling fluid out of the chamber 401 in order to purge any fluid that is carried from a previous location.

Figure 6:
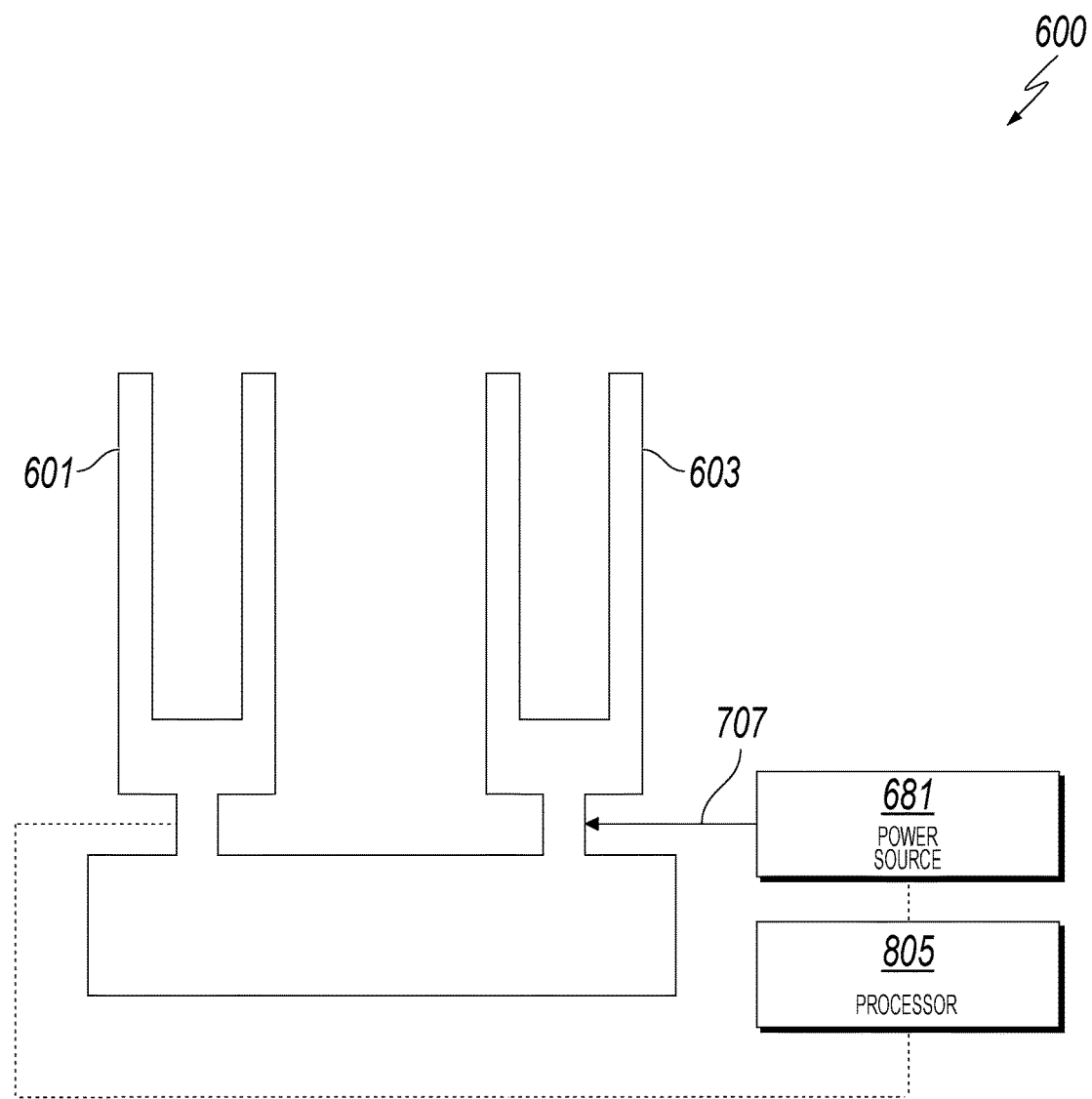
FIG. 6 is a diagram of an example tuning fork used in photoacoustic spectroscopy.

FIG. 6 illustrates an example of a dual QTF 600 that can be part of a QEPAS system 200. The QEPAS signal can be enhanced utilizing parametric amplification. The dual QTF 600 can include two tuning forks 601 and 603 that are mechanically coupled. The dimensions and size of the QTF 601 can vary, for example, from 3.2 to 20 millimeters (mm) in prong length, 0.25 to 0.8 mm in prong width, 0.34 to 1.4 mm in thickness, and 0.3 to 1 mm in prong spacing. In some implementations, QTF 601 can be a first, passive signal detector of a QEPAS system 200 that can detect an induced pressure wave in the gas sample. The QEPAS system 200 can include a power source 681 that can provide a current 707 to a second, active QTF 603, that can serve as the signal amplifier and can be driven non-linearly and induce a pressure wave in the gas sample. The processor 805 (described in more detail later) can receive a signal from the first, passive QTF 601. In response to the signal from the first, passive QTF 601, the processor 805 can transmit a signal to the power source 681 that provides the current 707 to the second, active QTF 603. The dual QTF 600 can be described as a coupled resonating system where tuning fork 601 has a frequency f, and tuning fork 603 has a frequency 2f. In some implementations, a resonator or amplifier can be made of magnetic material and embedded in a varying magnetic field to enhance the resonance and therefore, the QEPAS signal. Parametric amplification can enhance resonance, especially in cases where the QEPAS signal can be degraded, such as when the sample gas is wet. In downhole conditions, gases such as methane can be wet, for example 100% saturation of methane. The QEPAS signal can also be degraded when the sample gas is at a greater pressure than atmospheric pressure. Another case in which the QEPAS signal can be degraded is when the sample gas includes large concentrations of a gas, such as in gas wells, where the methane concentration can be approximately 60% to 80% or even greater.

The tunability of lasers, such as QCLs, can be combined with various modulation techniques to allow a spectroscopic gas sensor, such as a QEPAS, to reach detection sensitivities, for example, on the order of parts per trillion compositions of components. Amplitude modulation (AM) can include switching a laser injection current to a laser, for example QEPAS laser 201, between on state and off state by a signal modulator or optically chopping the light or laser beam 202 emitted by the laser 201 with an optical chopper. Wavelength modulation (WM) can include modulating the frequency of the light or laser beam 202 by a signal modulator with a periodic function, such as a sine wave. WM inherently modulates frequency, as wavelength is the inverse of frequency. With WM, any noise centered at the QTF 207 detection frequency and within the detection bandwidth or range can affect trace gas measurements, and noise outside the detection bandwidth do not. The interaction between the chemical components to be detected and the modulated light or laser beam 202 can lead to a generation of signals at the modulation frequency and its harmonics. Each harmonic of the analytical WM signal can be detected with phase-sensitive detection devices, such as a lock-in amplifier. For gas sensing techniques based on cavity-enhanced and multi-pass absorption cell, the choice of modulation frequency can be limited by the detection bandwidth. The detection bandwidth can be chosen to limit 1/f laser noise, but exceeding 100 kHz, for example, is not necessary because noise can level off at frequencies greater than or equal to approximately 100 kHz. With QEPAS, the modulation frequency matches the resonance frequency of the QTF 207 or its sub-harmonics, but resonance frequencies exceeding 40 kHz, for example, can be unsuitable, as they can exceed the vibration-translational relaxation rates of a target gas.

WM can include dithering the laser 201 injection current with a sine function, which can result in simultaneous AM and WM with a phase-shift that depends on the laser 201. The WM description can be based on an intensity representation of an optical wave, so that the absorption of the sample can be considered, and the dispersion effects due to the sample can be neglected. The WM description can be based on the instantaneous laser frequency:

$$v(t) = v_0 - \Delta\cos(\omega t) \quad (1)$$

where $v_0$ is the optical carrier frequency and $\omega = 2\pi f$ is the modulation angular frequency due to the laser injection current that is modulated at the same angular frequency.

In addition to frequency modulation, the current waveform applied to the laser 201, such as a QCL, can produce a sinusoidal modulation of the laser intensity:

$$I(t) = I_0 + \Delta I \cos(\omega t) \quad (2)$$

where the amplitude $\Delta I$ of the sinusoidal intensity modulation is determined by the slope of the laser power versus the current characteristics, which can be assumed constant across a wavelength scan.

The instantaneous laser frequency can interact with the absorption feature. The absorption coefficient $\alpha(v(t))$ for a small $\Delta v$ around the absorption feature considered can be expanded:

$$\alpha(v(t)) = \quad (3)$$
$$\alpha_0 + \left(\frac{\partial\alpha}{\partial v}\bigg|v=v_0\right)\Delta v\cos(\omega t) + \frac{1}{2}\left(\frac{\partial^2\alpha}{\partial v^2}\bigg|v=v_0\right)(\Delta v)^2\cos^2(\omega t) + \ldots$$

where $\alpha_0$ can be considered to be the background absorption contribution. The laser 201 can be modulated both in intensity and in wavelength simultaneously. From the Lambert-Beer law, a small absorption $I_{abs}$ can be expressed as:

$$I_{abs}(t) = (I_0 + \Delta I\cos(\omega t)) \quad (4)$$
$$\left[1 - L\left(\alpha_0 + \left(\frac{\partial\alpha}{\partial v}\bigg|_{v=v_0}\right)\Delta v\cos(\omega t) + \frac{1}{2}\left(\frac{\partial^2\alpha}{\partial v^2}\bigg|_{v=v_0}\right)(\Delta v)^2\cos^2(\omega t)\right)\right]$$

where L is the effective length over which the absorption takes place to produce an acoustic wave that can be detected by the QTF 207. L can be comparable to the thickness of the QTF 207. The $1\omega$-signal, $S_{1\omega}$, can be expressed as:

$$S_{1\omega} = L\Delta I\alpha_0 - L\left(\frac{\partial\alpha}{\partial v}\bigg|_{v=v_0}\right)\Delta v \quad (5)$$

and the $2\omega$-signal, $S_{2\omega}$, can be expressed as:

$$S_{2\omega} = -L\Delta I\frac{\partial\alpha}{\partial v}\bigg|_{v=v_0}\Delta v + \frac{I_0}{2}\left(\frac{\partial^2\alpha}{\partial v^2}\bigg|_{v=v_0}\right)(\Delta v)^2 \quad (6)$$

Referring to Eqs. 5 and 6, the background absorption $\alpha_0$ contributes to $S_{1\omega}$ and does not contribute to $S_{2\omega}$. If the absorption coefficient is assumed to have a pure Lorentzian line shape, $S_{1\omega}$ can have a pure first derivative line shape with constant background, and $S_{2\omega}$ can include two terms—a first term from a residual amplitude modulation that is proportional to the first derivative, and a second term from a laser wavelength modulation. $S_{2\omega}$ is not a pure second derivative of the Lorentzian line shape and is distorted by a contribution from the residual amplitude modulation. This distortion does not affect the peak position of $S_{2\omega}$ because the first derivative of the Lorentzian line shape vanishes when $v=v_0$.

The QEPAS signal can be demodulated by utilizing a lock-in amplifier at the fundamental frequency f or its successive harmonics nf. When the laser beam 202 is modulated at a resonance frequency $f_0$, and the QEPAS signal is demodulated at the same frequency, the demodulated signal can be called the 1f-QEPAS signal. When the laser beam 202 is modulated at a resonance frequency $f_0/2$, and the QEPAS signal is demodulated at $f_0$, the demodulated signal can be called the 2f-QEPAS signal. In the case of the 2f-QEPAS approach, the QTF 207 can detect sound oscillations at the second harmonic of the modulation frequency caused by a double intersection of the absorption line by the laser beam 202 during a modulation period.

A strong background signal can be observed for the 1f-QEPAS approach, originating from stray light from the walls of the chamber 401. The amplitude of the offset can increase with increased misalignment of the laser beam 202 in lateral directions, so that the beam 202 tails touch the QTF 207. The 2f-QEPAS approach can be background-free. Distortions in a demodulated signal displaying asymmetry on both sides of the spectrum around a peak can be attributed to an amplitude-intrinsic modulation contribution, which can be introduced by current modulation. The WM amplitude $\Delta f$ and light intensity modulation $\Delta I$ can be manipulated to improve a 2f-QEPAS signal at various sample gas pressures.

Figure 7:
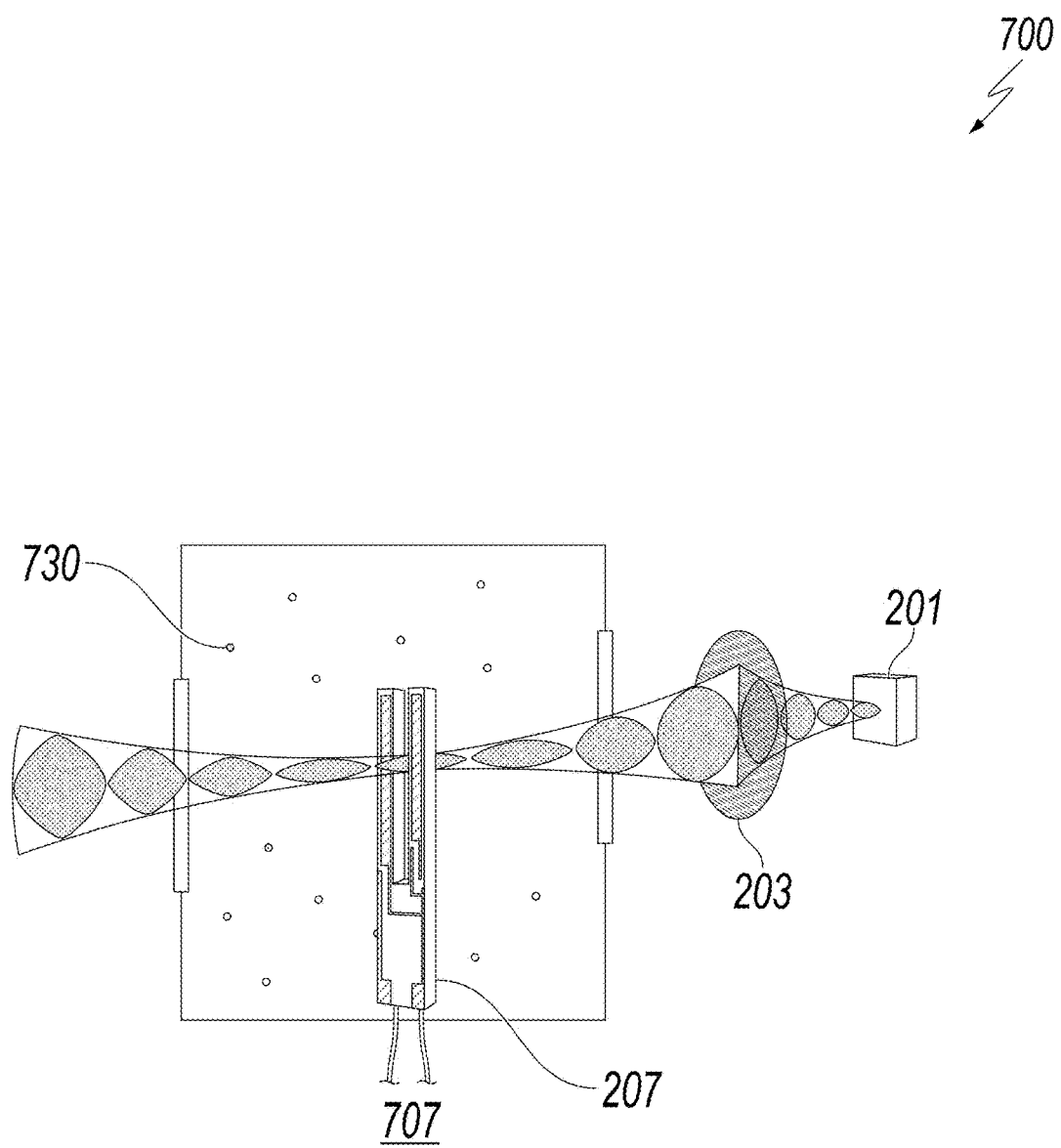
FIG. 7 is a schematic diagram of an example active tuning of a tuning fork used in photoacoustic spectroscopy.

In some implementations, the QTF 207 can be actively driven with a current as the QTF 207 detects a photoacoustic signal. FIG. 7 is a schematic diagram of an example of an actively driven QTF 207. The laser source 201 produces a laser beam that can be modulated. The laser beam passes through the lens 203 and induces a pressure wave in a target gas 730, such as methane. The tuning fork 207 detects the photoacoustic signal from the vibration of its prongs due to the induced pressure wave. In the case that the tuning fork 207 is actively driven with a current e(t) as it detects a photoacoustic x(t), according to the superposition principle, the received signal y(t) is:

$$y(t) = x(t) + e(t) \quad (7)$$

By actuating (or actively driving) the tuning fork with a current 707, the photoacoustic signal can be modulated and shifted to a passband where: the signals associated with various gas peaks can be more easily separated; the signal versus noise ratio (SNR) can be improved, that is, increased at the passband in comparison to the noise floor; the actuation frequency can be tuned to achieve a better signal; and a closed loop can be formed to compensate for pressure or temperature drift in the gas sample. The physical limit in the QEPAS system 200 detection is set by the thermal noise of the QTF 207 due to its resistance. QTF 207 (or resonator) resistance values can typically be on the order of magnitude of hundreds of kilo-ohms (kΩ), which can result in a thermal noise signal processed by a lock-in amplifier that is less than 1 microvolt (μV). In some implementations, the total noise given by the electrical component introduced by amplification stages and the optical component due to photothermal heating of the prongs by the laser beam 202, can be kept as small as a few μV.

The driving current or excitation signal e(t) can be of any general form, for example, harmonic form. If the tuning fork 207 active excitation frequency is $\omega_e$, then the excitation signal e(t) to the tuning fork 207 can be expressed as:

$$e(t) = \alpha_e \cos(\omega_e t + \phi_e) \quad (8)$$

where $\alpha_e$ and $\phi_e$ are the magnitude and initial phase, respectively. Similarly, the photoacoustic signal can be expressed as:

$$x(t) = \alpha_x \cos(\omega_x t + \phi_x) \quad (9)$$

Assuming there also exists noise n(t) in the received signal, the received signal y(t) can be expressed as:

$$\begin{aligned} y(t) &= x(t) + e(t) + n(t) \\ &= a_x \cos(\omega_x t + \phi_x) + a_e \cos(\omega_e t + \phi_e) + n(t) \end{aligned} \quad (10)$$

The demodulated signal z(t) can be obtained by multiplying the received signal y(t) by the excitation harmonic signal:

$$\begin{aligned} z(t) &= y(t)\cos(\omega_e t) \\ &= [x(t) + e(t) + n(t)]\cos(\omega_e t) \\ &= [a_x \cos(\omega_x t + \phi_x) + a_e \cos(\omega_e t + \phi_e) + n(t)] \\ &\quad \cos(\omega_e t) \end{aligned} \quad (11)$$

With trigonometric manipulation, the demodulated signal z(t) can also be expressed as:

$$z(t) = \frac{a_x}{2}[\cos((\omega_x - \omega_e)t + \phi_x) + \cos((\omega_x + \omega_e)t + \phi_x)] + \frac{a_e}{2}[\cos(\phi_e) + \cos(2\omega_e t + \phi_e)] + n(t)\cos(\omega_e t) \quad (12)$$

Referring to Eq. 12, only the terms within the first set of square brackets contain information about the photoacoustic signal, where the first term is located at a lesser frequency band corresponding to the difference between $\omega_x$ and $\omega_e$, and the second term is at a greater frequency of $\omega_x + \omega_e$, either one of which can be separated from the other by filtering the photoacoustic signal z(t). In QEPAS applications, $\omega_x$ is generally determined by the photoacoustic effect following gas absorption of the laser energy, and is therefore associated with the molecular properties of the target gas 730. With the active modulation scheme with driving current e(t), $\omega_e$ becomes the design parameter that can be chosen adaptively to increase SNR and improve tuning. In the case of photoacoustic signal drift due to temperature or pressure effects as the sample gas is subjected to laser illumination, $\omega_e$ can be adaptively adjusted to determine the amount or extent of frequency drifting and utilize that information to tune the laser source 201 to compensate accordingly. This adaptive pressure and temperature compensation can effectively form a closed feedback loop to iteratively adjust the laser frequency at which the target gas 730 molecules are excited in order to fine-tune the laser 201 and achieve greater sensitivities. The closed feedback loop can also be applicable to the dual QTF 600 shown in FIG. 6.

Figure 8:
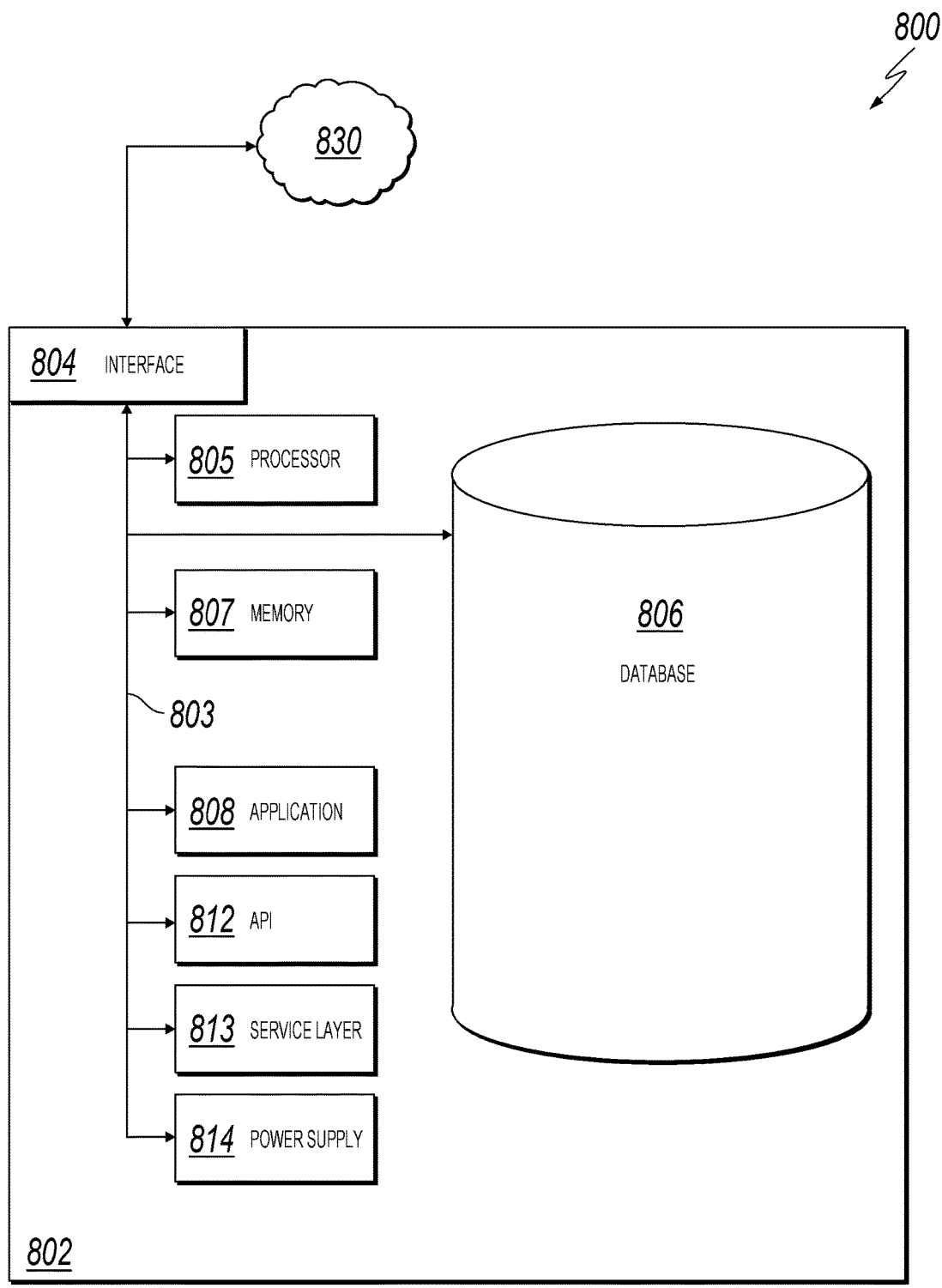
FIG. 8 is a block diagram illustrating an example computer system.

FIG. 8 is a block diagram of an example computer system 800 used to provide computational functionalities associated with described algorithms, methods, functions, processes, flows, and procedures, as described in the instant disclosure, according to an implementation. The illustrated computer 802 is intended to encompass any computing device such as a server, desktop computer, laptop/notebook computer, wireless data port, smart phone, personal data assistant (PDA), tablet computing device, one or more processors within these devices, and physical or virtual instances (or both) of the computing device. Additionally, the computer 802 can include an input device that can accept user information, such as a keypad, keyboard, or touch screen and an output device that conveys information associated with the operation of the computer 802, such as digital data, visual, or audio information (or a combination of information), or a graphical user interface (GUI).

The computer 802 can serve in a role, for example, as a client, network component, a server, a database, or a combination of roles of a computer system for performing the subject matter described in the instant disclosure. The illustrated computer 802 is communicably coupled with a network 830. In some implementations, one or more components of the computer 802 can be configured to operate within environments, such as a cloud-computing-based environment, local environment, global environment, or combinations of these.

In summary, the computer 802 is an electronic computing device operable to receive, transmit, process, store, or manage data and information associated with the described subject matter. According to some implementations, the computer 802 can also include or be communicably coupled with an application server, e-mail server, web server, caching server, streaming data server, or a combination of servers.

The computer 802 can receive requests over network 830 from a client application (for example, executing on another computer 802) and respond to the received requests by processing the received requests using an appropriate software application(s). In addition, requests can also be sent to the computer 802 from internal users (for example, from a command console), external users, third-parties, or combinations of these.

Each of the components of the computer 802 can communicate using a system bus 803. In some implementations, any or all of the components of the computer 802, hardware or software (or a combination of both hardware and software), can interface with each other or the interface 804 (or a combination of both), over the system bus 803 using an application programming interface (API) 812 or a service layer 813 (or a combination of the API 812 and service layer 813). The API 812 can include specifications for routines, data structures, and object classes. The API 812 can be either computer-language independent or dependent and refer to a complete interface, a single function, or even a set of APIs. The service layer 813 provides software services to the computer 802 or other components (whether or not illustrated) that are communicably coupled to the computer 802. The functionality of the computer 802 can be accessible for all service consumers using this service layer. Software services, such as those provided by the service layer 813, provide reusable, defined functionalities through a defined interface. For example, the interface can be software written in JAVA or C++. While illustrated as an integrated component of the computer 802, some implementations can illustrate the API 812 or the service layer 813 as stand-alone components in relation to other components of the computer 802 or other components (whether or not illustrated) that are communicably coupled to the computer 802. Moreover, any or all parts of the API 812 or the service layer 813 can be implemented as child or sub-modules of another software module, enterprise application, or hardware module without departing from the scope of this disclosure.

The computer 802 includes an interface 804. Although illustrated as a single interface 804 in FIG. 8, two or more interfaces 804 can be used according to particular needs, desires, or particular implementations of the computer 802. The interface 804 is used by the computer 802 for communicating with other systems that are connected to the network 830 (whether illustrated or not) in a distributed environment. Generally, the interface 804 comprises logic encoded in software or hardware (or a combination of software and hardware) and is operable to communicate with the network 830. More specifically, the interface 804 can comprise software supporting one or more communication protocols associated with communications such that the network 830 or interface's hardware is operable to communicate physical signals within and outside of the illustrated computer 802.

The computer 802 includes a processor 805. Although illustrated as a single processor 805 in FIG. 8, two or more processors can be used according to particular needs, desires, or particular implementations of the computer 802. Generally, the processor 805 executes instructions and manipulates data to perform the operations of the computer 802 and any algorithms, methods, functions, processes, flows, and procedures as described in the instant disclosure.

The computer 802 also includes a database 806 that can store data for the computer 802 or other components (or a combination of both) that can be connected to the network 830 (whether illustrated or not). For example, database 806 can be an in-memory or conventional. In some implementations, database 806 can be a combination of two or more different database types (for example, a hybrid in-memory and conventional database) according to particular needs, desires, or particular implementations of the computer 802 and the described functionality. Although illustrated as a single database 806 in FIG. 8, two or more databases (of the same or combination of types) can be used according to particular needs, desires, or particular implementations of the computer 802 and the described functionality. While database 806 is illustrated as an integral component of the computer 802, in some implementations, database 806 can be external to the computer 802.

The computer 802 also includes a memory 807 that can store data for the computer 802 or other components (or a combination of both) that can be connected to the network 830 (whether illustrated or not). For example, memory 807 can be random access memory (RAM), read-only memory (ROM), optical memory, or magnetic memory storing data consistent with this disclosure. In some implementations, memory 807 can be a combination of two or more different types of memory (for example, a combination of RAM and magnetic storage) according to particular needs, desires, or particular implementations of the computer 802 and the described functionality. Although illustrated as a single memory 807 in FIG. 8, two or more memories 807 (of the same or combination of types) can be used according to particular needs, desires, or particular implementations of the computer 802 and the described functionality. While memory 807 is illustrated as an integral component of the computer 802, in some implementations, memory 807 can be external to the computer 802.

The application 808 is an algorithmic software engine providing functionality according to particular needs, desires, or particular implementations of the computer 802, particularly with respect to functionality described in this disclosure. For example, application 808 can serve as one or more components, modules, or applications. Further, although illustrated as a single application 808, the application 808 can be implemented as multiple applications 808 on the computer 802. In addition, although illustrated as integral to the computer 802, in some implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion or management circuits (such as recharging and standby). In some implementations, the power-supply 814 can include a power plug to allow the computer 802 to be plugged into a power source (such as a wall socket) to power, for example, the computer 802 or recharge a rechargeable battery.

There can be any number of computers 802 associated with, or external to, a computer system containing computer 802, each computer 802 communicating over network 830. Further, the term "client," "user," and other appropriate terminology can be used interchangeably, as appropriate, without departing from the scope of this disclosure. Moreover, this disclosure contemplates that many users can use one computer 802, or that one user can use multiple computers 802.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second, or less than 5 seconds. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, for example, a central processing unit (CPU), an FPGA (field programmable gate array), or an ASIC (application-specific integrated circuit). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code can be written in any form of programming language, including compiled or interpreted languages, or declarative or procedural languages, and it can be deployed in any form, such as a stand-alone program, a module, component, or subroutine. A computer program can, but need not, correspond to a file in a file system. A program can be stored in a portion of a file that stores other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs can instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM), or both. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, such as a mobile telephone, a personal digital assistant (PDA), a mobile audio or video player, a game console, a global positioning system (GPS) receiver, or a portable storage device (for example, a universal serial bus (USB) flash drive).

Computer-readable media (transitory or non-transitory, as appropriate) suitable for storing computer program instructions and data includes all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/-R, DVD-RAM, and DVD-ROM disks. The memory can store various objects or data, such as caches, classes, frameworks, applications, backup data, jobs, web pages, web page templates, database tables, and repositories storing dynamic information. The data can include, for example, parameters, variables, algorithms, instructions, rules, constraints, references, or combinations of these. Additionally, the memory can include any other appropriate data, such as logs, policies, security or access data, and reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity or a multi-touch screen using capacitive or electric sensing. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20), all or a portion of the Internet, or communication systems at one or more locations (or a combination of communication networks). The network can communicate with, for example, Internet Protocol (IP) packets, Frame Relay frames, Asynchronous Transfer Mode (ATM) cells, voice, video, or data between network addresses.

The computing system can include clients and servers. A client and server are generally remote from each other and typically interact through a communication network. The relationship of client and server arises by virtue of computer programs running on the respective computers and having a client-server relationship to each other.

This description is presented to enable any person skilled in the art to make and use the disclosed subject matter in the context of one or more particular implementations. Various modifications, alterations, and permutations of the disclosed implementations can be made and will be readily apparent to those or ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

While this specification contains many specific implementation details, these should not be construed as limitations on the scope of the subject matter or on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A downhole system comprising:
  a quartz enhanced photoacoustic spectrometer (QEPAS) configured to be positioned within a wellbore formed in a subterranean zone of a hydrocarbon formation, the QEPAS comprising:
    a laser configured to emit light;
    a first, passive quartz tuning fork (QTF) configured to detect a pressure wave created in a gas, wherein the pressure wave is created as the light is absorbed by the gas; and
    a second, active QTF configured to amplify the pressure wave in the gas, wherein the first, passive QTF is configured to detect the amplified pressure wave;
  a sampling system coupled to the QEPAS, the sampling system configured to be positioned in the wellbore, the sampling system configured to obtain a sample of a wellbore fluid at a downhole location in the subterranean zone, the QEPAS configured to spectroscopically scan the sample and to determine a plurality of quantities of a corresponding plurality of hydrocarbons in the sample; and
  a computer system connected to the QEPAS, the computer system comprising:
    one or more processors; and a computer-readable medium storing instructions executable by the one or more processors to perform operations comprising:
  receiving the plurality of quantities of the plurality of hydrocarbons in the sample; and
  determining a plurality of ratios, each ratio being a ratio of one of the plurality of hydrocarbons with another of the plurality of hydrocarbons.

2. The system of claim 1, wherein the operations further comprise:
  receiving the plurality of ratios as an input to a design simulation of the hydrocarbon formation; and
  computationally simulating the hydrocarbon formation based, in part, on the plurality of ratios.

3. The system of claim 1, wherein the laser is configured to emit light at a wavelength range at which the plurality of hydrocarbons in the sample are simultaneously detectable.

4. The system of claim 1, wherein the QEPAS comprises a plurality of lasers, each configured to emit light at a respective wavelength at which a respective hydrocarbon of the plurality of hydrocarbons in the sample is detectable.

5. The system of claim 1, wherein the QEPAS comprises a hydrogen sulfide (H2S) laser configured to emit light at a wavelength at which H2S in the sample is detectable.

6. The system of claim 1, wherein the QEPAS comprises a signal modulator configured to periodically switch a laser injection current to the laser between an on state and an off state or an optical chopper to optically chop the light emitted by the laser.

7. The system of claim 6, wherein the signal modulator is configured to generate a periodic function to modulate a frequency of the light.

8. The system of claim 1, wherein a quality factor (Q factor) of at least one of the first, passive QTF and the second, active QTF is of the order of tens of thousands.

9. The system of claim 1, further comprising a power source connected to the processer, wherein the power source is configured to drive the second, active QTF in response to receiving a signal from the processor.

10. The system of claim 9, wherein the processor is configured to transmit the signal to the second, active QTF based on a signal received from the first, passive QTF.

11. The system of claim 1, further comprising a temperature controller configured to maintain a temperature of the QEPAS.

12. The system of claim 1, wherein the sampling system comprises:
  a chamber;
  a piston positioned within the chamber, the piston sealing an inner surface of the chamber to define a sample receiving volume, wherein the first, passive QTF and the second, active QTF are positioned within the sample receiving volume;
  an inlet valve fluidically connected to a chamber inlet, wherein a retraction of the piston in the sample receiving volume and an opening of the inlet valve causes the sample to flow into the sample receiving volume; and
  an outlet valve fluidically connected to a chamber outlet, wherein an advancement of the piston in the sample receiving volume and an opening of the outlet valve causes the sample to flow out of the sample receiving volume.

13. The system of claim 12, wherein the sample is a two-phase sample comprising a gas and a liquid, wherein the inlet valve is configured to de-pressurize the sample to separate the gas from the liquid, wherein the gas rises to an upper portion of the sample receiving volume and the liquid resides in a lower portion of the sample receiving volume, the QEPAS configured to spectroscopically scan the gas in the upper portion.

* * * * *